(12) United States Patent
Loibner et al.

(10) Patent No.: US 6,956,119 B2
(45) Date of Patent: Oct. 18, 2005

(54) POLYSACCHARIDE-POLYPEPTIDE CONJUGATE

(75) Inventors: Hans Loibner, Heimgasse 23, A-1238 Vienna (AT); Helmut Eckert, Oberwil (CH)

(73) Assignee: Hans Loibner, Vienna (AT)

( * ) Notice: Subject to any disclaimer, the term of this patent is extended or adjusted under 35 U.S.C. 154(b) by 1 day.

(21) Appl. No.: 10/221,785

(22) PCT Filed: Mar. 21, 2001

(86) PCT No.: PCT/AT01/00079
§ 371 (c)(1),
(2), (4) Date: Sep. 17, 2002

(87) PCT Pub. No.: WO01/70272
PCT Pub. Date: Sep. 27, 2001

(65) Prior Publication Data
US 2003/0120033 A1 Jun. 26, 2003

(30) Foreign Application Priority Data
Mar. 21, 2000 (AT) ........................ A 471/2000

(51) Int. Cl.⁷ ................................ C07K 9/00
(52) U.S. Cl. ................ 536/123.1; 536/1.11; 536/53; 530/22; 530/322; 530/395; 514/8; 424/130.1; 424/137.1
(58) Field of Search ................ 530/322, 395, 530/387.5, 387.1; 536/53; 424/130.1, 137.1

(56) References Cited

U.S. PATENT DOCUMENTS

| 5,554,730 A | * | 9/1996 | Woiszwillo et al. ........ 530/410 |
| 5,846,951 A | | 12/1998 | Gregoriadis |
| 5,989,552 A | * | 11/1999 | McKenzie et al. ....... 424/185.1 |
| 6,011,008 A | * | 1/2000 | Domb et al. .................. 514/8 |

FOREIGN PATENT DOCUMENTS

| DE | 198 21 859 | 12/1999 |
| SU | 730 694 | 4/1980 |
| WO | 96 20012 | 7/1996 |
| WO | 99 49897 | 10/1999 |
| WO | 99 55715 | 11/1999 |

OTHER PUBLICATIONS

Fagnani et al, Cancer Research, 1990, 50, 3638–3645.*
Mehvar, R., Journal of Controlled Relaese, 2000, 69 1–25.*
R. Mehvar: "Dextrans for targeted and sustained delivery of therapeutic and imaging agents" Journal of Controlled Release, vol. 69, No. 1, pp. 1–25 Oct. 3, 2000.

* cited by examiner

Primary Examiner—James O. Wilson
Assistant Examiner—Ganapathy Krishnan
(74) Attorney, Agent, or Firm—Oblon, Spivak, McClelland, Maier & Neustadt, P.C.

(57) ABSTRACT

Disclosed is a method of producing a polysaccharide-polypeptide conjugate by reacting a polysaccharide with a polypeptide which contains at least one free amino group, wherein a polysaccharide carrier comprising vicinal hydroxyl groups is oxidized under ring opening to create vicinal aldehyde groups and is reacted with one or more base-instable antigenic polypeptide(s) containing at least one free amino group, the polypeptide(s) being bound directly to the polysaccharide carrier via at least one azomethine bond.

19 Claims, 1 Drawing Sheet

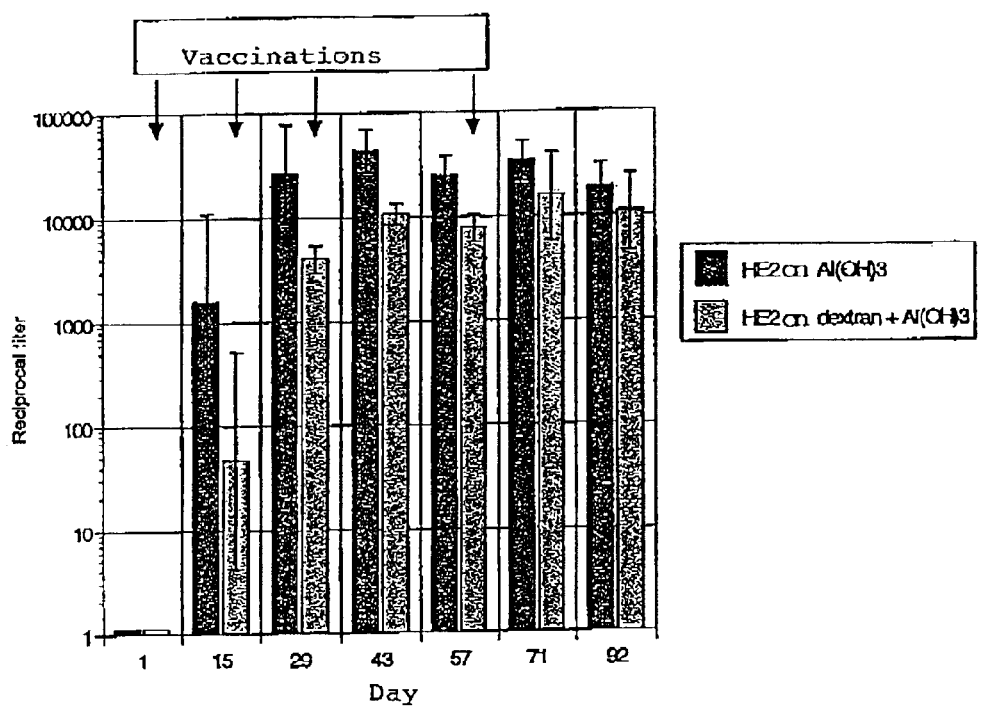
Fig. 1: Induction of Antibodies Against HE2 (ELISA) in Rhesus Monkeys — Comparison of Two Formulations

POLYSACCHARIDE-POLYPEPTIDE CONJUGATE

The present invention relates to a new use of oxidized polysaccharides as a carrier material for components of vaccines, in particular to a method of producing a polysaccharide-polypeptide conjugate by reacting a polysaccharide with a polypeptide comprising at least one free amino group, as well as to the use of such a conjugate as a vaccine.

Vaccines are characterized in that one or more antigens are administered in an immunogenic formulation in a small amount, mostly parenteral (subcutaneously or intramuscularly) so as to trigger a strong and protective immune response. At present, most vaccines are produced for protecting against microbial infections. In these instances, the antigens used are inactivated and altered microorganisms or parts thereof, or defined proteins from such microorganisms which are suitable to trigger an immune response against the respective microorganism.

For years also the effectiveness of many experimental vaccines against other diseases has been investigated. Among them are vaccines against cancer. In this case, the immune system of cancer patients is to be selectively activated so as to combat malignant cells. This is attempted by means of the most differing approaches. Among them are vaccinations with autologous or allogenic tumor cells, chemically or molecular-biologically modified autologous or allogenic tumor cells, isolated tumor-associated antigens (TAA) or tumor-associated antigens prepared by chemical or molecular-biological methods, peptides derived therefrom, anti-idiotypical antibodies as a surrogate of a TAA, lately also vaccinations with DNA which codes for TAA or for structures derived therefrom, etc. In principle, very small amounts of a suitable vaccine will suffice to induce an immunity from months up to years, since the attenuation can be boosted by booster vaccinations. Moreover, in an active immunization both a humoral and a cellular immunity can be induced the interaction of which can yield an effective protection against cancer.

To attain a strong immunity, antigens in vaccines mostly are administered together with an adjuvant. As examples of adjuvants the following may be mentioned, without, however, being restricted thereto: aluminum hydroxide (Alu-Gel), derivatives of lipopolysaccharide, Bacillus Calmette Guerin (BCG), liposome preparations, formulations with additional antigens against which the immune system has already produced a pronounced immune response, such as, e.g., tetanus toxoid, Pseudomonas exotoxin or components of influenza viruses, optionally in a liposome preparation. Furthermore, it is known that the immune response may also be enhanced by simultaneously administering endogenous proteins which play an important role in the build-up of an immune response, such as, e.g., granulocyte macrophages-stimulating factor (GM-CSF), interleukin 2 (IL-2), interleukin 12 (IL-12) or gamma interferon (IFNγ).

U.S. Pat. No. 5,554,730-B relates to polysaccharide-protein conjugates, wherein a particulate vaccine is to be created. For this purpose, a polysaccharide-protein conjugate is created as a Schiff's base (azomethin), primarily by reacting a protein carrier with an oxidized polysaccharide antigen in the presence of a "crowding agent" (water displacing agent), wherein the protein carrier is immediately denatured due to the presence of the crowding agent, and the conjugate precipitates in the form of microparticles. Although a dissolution of the precipitated microparticles in a strongly basic environment (0.1 N NaOH) for obtaining a vaccination solution as such is possible and has also been disclosed, it only makes sense if a polysaccharide antigen is used, because any antigenic protein would have lost its antigenic determinants as a consequence of denaturing, and thus would no longer be effective.

WO 99/55715 describes polysaccharide-antigen conjugates in which the antigen is either bound to the polysaccharide via a suitable bivalent linker, or via a terminal aldehyde group. A direct binding of the antigen to the polysaccharide via an azomethin bond thus is limited to the number of the terminal aldehyde groups present in the polysaccharide.

Also DE-198 21 859-A1 describes polysaccharide-antigen conjugates, wherein a suitable crosslinker is bound in the polysaccharide by means of an azomethin bond to aldehyde functions obtained by periodate oxidation. In the cross-linker, a maleimido function is additionally provided, to which an —SH group of cysteine can add. The utilized antigens then are N- or C-terminally provided with an additional Cys so as to allow for the addition of the terminal SH function with the cross-linker and thus the obtaining of the polysaccharide-antigen conjugates described.

Finally, U.S. Pat. No. 5,846,951 relates to polysaccharides comprising at least 5 sialic acid residues which polysaccharides can be provided with terminal aldehyde groups at the non-reducing ends of the polysialic acids by means of oxidation with sodium periodate. Terminal aldehyde groups created in this manner may then bind amino-group-containing medicaments, e.g proteins, via azomethine bonds.

Most antigens used for vaccines comprise structures with primary amino groups. In particular, all protein antigens normally comprise at least one, but mostly several, lysines in their amino acid sequence. The amino groups of these lysines are present in free form.

It has long been known that primary amines can react with aldehydes. The product of this reaction is called Schiff's base. Schiff's bases are not completely stable compounds, they can be hydrolyzed under suitable conditions and thus be returned into their starting substances.

Furthermore, it has been known that compounds comprising vicinal hydroxyl groups can be oxidized with the help of suitable oxidants, in particular with periodic acid or salts of periodic acid, such as sodium metaperiodate, such that two aldehyde functions are formed by breaking the C—C bond on which the neighboring hydroxyl groups are located.

A large number of high-molecular polysaccharides consist of monomeric sugar units which carry vicinal hydroxyl groups. Dextrane and mannan should be mentioned as two non-limiting examples. Such polysaccharides thus can be oxidized with periodate in the above-described manner without the bonds between the monomers being split. If, based on the number of monomeric units, a stoichiometric smaller amount of periodate is used, the oxidation will occur only partially, which means that only so many monomers will be oxidized according to the principle of random as corresponds to the amount of periodate.

The present invention is based on the object of providing further means and methods which will lead to immunogenic formulations of vaccines.

In a method of the initially defined type, this object is achieved in that a polysaccharide carrier comprising vicinal hydroxyl groups is oxidized under ring opening to create vicinal aldehyde groups, and is reacted with one or several base-instable antigenic polypeptide(s) containing at least one free amino group, wherein the polypeptide(s) is (are)

bound directly to the polysaccharide carrier via at least one azomethine bond. Partially oxidized polysaccharides thus are a suitable carrier material for the formulation of vaccines if the utilized base-instable antigenic polypeptides comprise one or more free primary amino groups and thus, via an azomethine bond, can be connected with the vicinal aldehyde groups created in the carrier material by ring opening. Preferably, the base-instable antigenic polypeptides used according to the invention are stable up to a pH of approximately 11, preferably up to a pH of approximately 10, still more preferred up to a pH of approximately 9, most preferred up to a pH of approximately 8. If polypeptides are mentioned in the context of the present invention, proteins having at least 6 amino acids in the chain are to be understood. In the same way, polysaccharides are understood to be poly-sugars comprising at least 3 monomer units in the chain. Preferably used polysaccharides are mannan, e.g. having a molecular weight of at least 70 kDa, and dextrane, e.g. having a molecular weight of at least 70 kDa, particularly preferred having a molecular weight of approximately 2000 kDa.

According to a preferred embodiment of the present invention, the vicinal hydroxyl groups originally present in the polysaccharide carrier are at least partially oxidized, preferably by at least 20%. By controlling the rate of oxidation, e.g. by a stoichiometric smaller amount of oxidating agent, the amount of aldehyde groups available for an azomethine bond between carrier and polypeptide can easily be adjusted.

Preferably, the base-instable antigenic polypeptide is a vaccine antigen, particularly preferred an antibody, e.g. a monoclonal antibody, such as the murine monoclonal antibody HE2. A new method of cancer vaccination has been described in application PCT/EP00/00174 (priority date: Jan. 13, 1999), "Verwendung von Antikörpern zur Vakzinierung gegen Krebs" ("The Use of Antibodies for Vaccinating against Cancer"), the disclosure of which is included herein by reference thereto. The monoclonal antibody HE2 described there which is used as the vaccine antigen in a cancer vaccination serves as a non-limiting example for the formulation of a vaccine according to the method of conjugation to a partially oxidized high-molecular polysaccharide described here.

According to a further preferred embodiment of the present invention, the base-instable antigenic polypeptide has the same binding fine specificity as the antibody HE2.

It is also suitable if in addition to the respective base-instable antigenic polypeptide substances are conjugated which cause an enhancement of the immune response, e.g. GM-CSF, IL-2, IL-12 or Gamma-Interferon, or a mixture of these substances.

Moreover, it is preferred if the polysaccharide-polypeptide conjugate according to the invention is additionally adsorbed on aluminum hydroxide and/or mixed with pharmaceutically acceptable carriers.

Finally, it is preferred if the polysaccharide-polypeptide conjugate obtained according to the invention is formulated as a vaccine formulation to be administered by subcutaneous, intradermal or intramuscular injection, e.g. by dissolving or suspending the optionally, e.g., aluminum-hydroxide-adsorbed conjugate in a suitable physiological buffer and the like.

In general, the following advantages and specific properties of the conjugate according to the invention should be mentioned:

The components coupled to the oxidized polysaccharides via primary amines (conjugate and adjuvants and additives, respectively) are slowly released in the presence of an excess of molecules with free primary amines, e.g. serum proteins. The slow release effect thus forming is desired for vaccines, since by this antigen-presenting cells are able to locally receive the vaccination antigens at the site of vaccination for a longer period of time.

By the choice of the polysaccharide, the properties of the conjugate can be influenced. This applies both to the molecular size of the polysaccharide and to its chemical composition. If, e.g., mannan is chosen as the polysaccharide, the corresponding conjugate preferably will be taken up by cells of the immune system which carry the mannose receptor. Among them are, in particular, macrophages and dendritic cells as professional antigen-presenting cells. In this manner, an increased immune response is attained.

Several components can simultaneously be bound to partially oxidized polysaccharides. These may be several differing vaccine antigens, or vaccine antigens together with components enhancing the immune response, such as, e.g., the proteins GM-CSF, IL-2, IL-12 or gamma interferon.

The enclosed FIG. 1 shows the comparison of two formulations as regards the induction of antibodies against HE2 (ELISA) in rhesus monkeys.

EXAMPLE

At first, dextrane having a molecular weight of 2000 kDa (SIGMA D-5376) is oxidized by 20% with sodium metaperiodate. For this purpose, 324 mg of dextrane are dissolved with stirring in 4 ml of distilled water. To this solution, 86 mg of sodium metaperiodate previously dissolved in 0.6 ml of distilled water are admixed, and incubated in the dark at 37° C. for 30 minutes. 25 mg of the antibody HE2 (PCT/EP00/00174) are brought to pH 7.4 with 1 M $Na_2HPO_4$, and 45 µl of a thimerosal solution (10 mg/ml) are added.

To this solution, 1.675 l of the above-obtained oxidized dextrane solution are added and incubated in the dark at 37° C. for 2 days. The completeness of the reaction is analytically checked by chromatography on a molecular weight column (zorbax 450). The signal corresponding to a molecular weight of 150 kDa (monomeric HE2) has disappeared, and in its place a signal occurs in the exclusion volume of the column which corresponds to a molecular weight of >2000 kDa.

The solution obtained is chromatographed by means of a preparative molecular weight column which is equilibrated with the final buffer (1 mM phosphate buffer in physiological saline, pH=5.5). The material obtained in the exclusion volume consists of the high-molecular conjugate of the antibody HE2 on partially oxidized dextrane. The content of conjugated HE2 can be determined by integration of the signal after analytical chromatography on a molecular weight column as compared to monomeric HE2. The solution obtained is mixed with an aqueous aluminum hydroxide such that the final concentration is 0.5 mg of HE2 on 1.67 mg of aluminum hydroxide in 0.5 ml of buffer.

Four rhesus monkeys are subcutaneously immunized with 0.5 ml of the above formulation on days 1, 15, 29 and 57. The sera of various points of time were assayed by means of ELISA for an induction of antibodies against monomeric HE2. As a comparison, four rhesus monkeys were vaccinated in the same manner with a standard formulation of 0.5 mg of monomeric HE2 adsorbed on 1.67 mg of aluminum hydroxide.

The ELISA was carried out as follows:

100 μl aliquots of the MAb HE2 (solution with 10 μg/ml in binding buffer) are incubated in the wells of a microtiter plate for 1 h at 37° C. After having washed the plate six times with washing buffer A, 200 μl each of blocking buffer A are added and incubated at 37° C. for 30 minutes. After washing the plate as described above, 100 μl aliquots each of the monkey sera to be tested are incubated in dilutions of 1:100 to 1:1 000 000 in dilution buffer A at 37° C. for 1 h. After having washed the plate as described above, 100 μl each of the peroxidase-conjugated goat anti-human-Ig antibody (Zymed) is added in a dilution of 1:1000 in dilution buffer A and incubated at 37° C. for 30 minutes. The plate is washed four times with washing buffer A, and twice with staining buffer. The antibody bond is detected by the addition of 100 μl each of the specific substrate, and the staining reaction is stopped after 10 minutes by adding 50 μl each of stopping solution. The evaluation is effected by measuring the optical density (OD) at 490 nm (wave length of the reference measurement is 620 nm).

The results of the ELISA are illustrated in FIG. 1. The animals vaccinated with the conjugate of HE2 on dextrane developed comparable titers of antibodies against HE2 as the monkeys vaccinated with the standard formulation.

Moreover, it was investigated to which extent HE2 after application can be found again in the serum of the monkeys. For this purpose, again an ELISA was used, which was carried out as follows:

100 μl aliquots of a purified polyclonal anti-idiotypic goat antibody against HE2 (solution with 10 μg/ml in binding buffer) are incubated in the wells of a microtiter plate at 37° C. for 1 h. After having washed the plate six times with washing buffer A, 200 μl each of the blocking buffer are admixed and incubated at 37° C. for 30 minutes. After having washed the plate as described above, 100 μl aliquots each of the monkey sera to be tested are incubated in dilutions of 1:4 to 1:100 000 in dilution buffer A at 37° C. for 1 h. After having washed the plate as described above, 100 μl each of a peroxidase-conjugated goat anti-mouse-IgG antibody (Zymed) are added in a dilution of 1:1000 in diluting buffer and incubated at 37° C. for 30 min. The plate is washed four times with washing buffer, and twice with staining buffer. The antibody bond is detected by the addition of 100 μl each of the specific substrate, and the staining reaction is stopped after 10 minutes by adding 50 μl each of stopping solution. The evaluation is effected by measuring the optical density (OD) at 490 nm (wave length of the reference measurement is 620 nm).

the results are illustrated in the following table:

| Time | Conjugate vaccine | Standard formulation |
| --- | --- | --- |
| 0 | 0; 0; 0; 0 ng/ml | 0; 0; 0; 0 ng/ml |
| 1 h | 0; 0; 0; 0 ng/ml | 13; 17; 74; 280 ng/ml |
| 4 h | 0; 0; 0; 0 ng/ml | 200, 280, 400, 740 ng/ml |
| 24 h | 0; 0; 0; 0 ng/ml | 960, 960, 1000, 740 ng/ml |

After 24 h, a trace of a HE2 concentration can be recognized in the serum of those animals which had been vaccinated with the conjugate, yet this concentration is below the detection limit of approximately 10 ng of HE2/ml serum. Apparently, the desorption of the vaccine antigen has clearly been reduced by the conjugation to partially oxidized dextrane, as compared to the standard formulation. Thereby probably fewer vaccinations will suffice to obtain a comparable titer than with a standard formulation on aluminum hydroxide.

| Materials used: | |
| --- | --- |
| Microtiter plates: | Immuno Plate F96 MaxiSorp (Nunc) for ELISA |
| Binding buffer: | 15 mM $Na_2CO_3$ |
| | 35 mM $NaHCO_3$ |
| | 3 mM $NaN_3$ |
| | pH: 9.6 |
| PBS deficient: | 138 mM NaCl |
| | 1.5 mM $KH_2PO_4$ |
| | 2.7 mM KCl |
| | 6.5 mM $Na_2HPO_4$ |
| | pH: 7.2 |
| Washing buffer: | 0.05% Tween 20 in PBS deficient |
| Blocking buffer: | 5% fetal calf serum (heat-inactivated) in PBS deficient |
| Dilution buffer: | 2% fetal calf serum (heat-inactivated) in PBS deficient |
| Staining buffer: | 24.3 mM citric acid |
| | 51.4 mM $Na_2HPO_4$ |
| | pH: 5.0 |
| Substrate: | 40 mg o-phenylene-diamine-dihydrochloride |
| | 100 ml staining buffer |
| | 20 μl $H_2O_2$ (30%) |
| Stopping solution: | 4 N $H_2SO_4$ |

What is claimed is:

1. A method of producing a polysaccharide-polypeptide conjugate, comprising:
    providing a polysaccharide carrier having vicinal hydroxyl groups,
    providing at least one antigenic polypeptide having at least one free amino group,
    partially oxidizing said polysaccharide carrier under ring opening so as to form vicinal aldehyde groups,
    reacting said oxidized polysaccharide carrier with said at least one antigenic polypeptide having the at least one free amino group, said at least one antigenic polypeptide being bound directly to said polysaccharide carrier via at least one azomethin bond thereby forming said polysaccharide-polypeptide conjugate.

2. The method of claim 1, wherein said partially oxidized polysaccharide carrier is oxidized by at least 20%.

3. The method of claim 1, wherein said at least one antigenic polypeptide is stable up to a pH of approximately 11.

4. The method of claim 1, wherein said at least one antigenic polypeptide is stable up to a pH of approximately 10.

5. The method of claim 1, wherein said at least one antigenic polypeptide is stable up to a pH of approximately 9.

6. The method of claim 1, wherein said at least one antigenic polypeptide is stable up to a pH of approximately 8.

7. The method of claim 1, wherein said polysaccharide is mannan.

8. The method of claim 7, wherein said mannan has a molecular weight of at least 70 kDa.

9. The method of claim 1, wherein said polysaccharide is dextrane.

10. The method of claim 9, wherein said dextrane has a molecular weight of at least 70 kDa.

11. The method of claim 9, wherein said dextrane has a molecular weight of approximately 2000 kDa.

12. The method of claim 1, wherein said antigenic polypeptide is a vaccine antigen.

13. The method of claim 12, wherein said vaccine antigen is an antibody.

14. The method of claim 13, wherein said antibody is a monoclonal antibody.

15. The method of claim 14, wherein said monoclonal antibody is a murine monoclonal antibody (HE2).

16. The method of claim 13, wherein said antibody has a binding fine specificity equal to the binding fine specificity of a murine monoclonal antibody (HE2).

17. The method of claim 1, further comprising providing immune-response-enhancing substances, and additionally conjugating said immune-response-enhancing substances to said antigenic polypeptide; wherein said immune-response-enhancing substances are selected from the group consisting of granulocyte macrophage colony-stimulating factor (GM-CFS), IL-2, IL-12, gamma interferon and mixtures thereof.

18. The method of claim 1, further comprising providing aluminum hydroxide and adsorbing said polysaccharide-polypeptide conjugate on said aluminum hydroxide.

19. The method of claim 1, further comprising providing a pharmaceutically acceptable carrier and mixing said formed polysaccharide-polypeptide conjugate with said pharmaceutically acceptable carrier.

* * * * *